United States Patent [19]

Ziman

[11] 4,336,059
[45] * Jun. 22, 1982

[54] HERBICIDAL AND PLANT-GROWTH-REGULATING N-(HETEROCYCLYL)-METHYLACETANILIDE

[75] Inventor: Stephen D. Ziman, San Francisco, Calif.

[73] Assignee: Chevron Research Company, San Francisco, Calif.

[*] Notice: The portion of the term of this patent subsequent to Sep. 9, 1997, has been disclaimed.

[21] Appl. No.: 134,378

[22] Filed: Mar. 27, 1980

Related U.S. Application Data

[63] Continuation of Ser. No. 10,877, Feb. 9, 1979, Pat. No. 4,221,584.

[51] Int. Cl.³ .................... A01N 43/78; C07D 277/28
[52] U.S. Cl. ........................................... 71/90; 71/76; 548/204
[58] Field of Search ............................ 71/90; 548/204

[56] References Cited

U.S. PATENT DOCUMENTS

| | | | |
|---|---|---|---|
| 3,907,544 | 9/1975 | Olin | 71/95 |
| 4,055,410 | 10/1977 | Cheng | 71/90 |
| 4,097,262 | 6/1978 | Cheng | 71/90 |
| 4,221,584 | 9/1980 | Ziman | 71/88 |
| 4,243,407 | 1/1981 | Caboy | 71/90 |

Primary Examiner—Catherine L. Mills
Attorney, Agent, or Firm—D. A. Newell; T. G. DeJonghe; G. F. Swiss

[57] ABSTRACT

Compounds of the formula

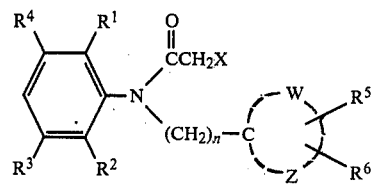

wherein $R^1$ is alkyl of 1 to 6 carbon atoms, alkoxy of 1 to 6 carbon atoms, alkenyl of 1 to 6 carbon atoms, haloalkyl of 1 to 2 carbon atoms and 1 to 3 of the same or different halogens selected from fluoro, chloro, bromo or iodo, nitro, hydroxy, alkoxyalkyl of 2 to 6 carbon atoms, fluoro, bromo, chloro or iodo, $R^2$, $R^3$ and $R^4$ are independently selected from hydrogen, alkyl of 1 to 6 carbon atoms, alkoxy of 1 to 6 carbon atoms, alkenyl of 1 to 6 carbon atoms, haloalkyl of 1 to 2 carbon atoms and 1 to 3 of the same or different halogens selected from fluoro, chloro, bromo or iodo, nitro, hydroxy, alkoxyalkyl of 2 to 6 carbon atoms, fluoro, bromo, chloro or iodo; $R^5$ and $R^6$ are independently selected from hydrogen, alkyl of 1 to 6 carbon atoms, alkoxy of 1 to 6 carbon atoms, alkenyl of 1 to 6 carbon atoms, alkoxyalkyl of 2 to 6 carbon atoms, phenyl and phenyl substituted with 1 to 5 of the same or different substituents selected from fluoro, chloro, bromo, alkyl of 1 to 4 carbon atoms or alkoxy of 1 to 4 carbon atoms; X is fluoro, bromo, chloro, iodo or alkoxy of 1 to 3 carbon atoms; W and Z are hetero atoms in an aromatic 5-membered ring independently selected from the group consisting of nitrogen, sulfur and oxygen; and $n=0$, 1 or 2, have herbicidal and plant growth regulating activity.

5 Claims, No Drawings

HERBICIDAL AND PLANT-GROWTH-REGULATING N-(HETEROCYCLYL)-METHYLACETANILIDE

This application is a continuation of Ser. No. 10,877, filed Feb. 9, 1979, now U.S. Pat. No. 4,221,584.

BACKGROUND OF THE INVENTION

The present invention relates to certain N-(heterocyclyl)-methylacetanilides and their use as herbicides.

U.S. Pat. No. 3,907,544 to John F. Olin discloses herbicidal 2-halo-N-(cyclicimidoalkylene)-substituted acetanilides.

U.S. Pat. Nos. 4,055,410, 4,097,262 and 4,104,051 to Jiin-Duey Cheng disclose herbicidal bromo- and chloro-acetamides containing oxo- and dioxocyclicimidoalkylene substituents.

German Offenlegungschrifft No. 2,704,281, published Aug. 3, 1978, and Belgian Pat. No. 863,565, issued Aug. 2, 1978, disclose herbicidal N-heterocyclylmethyl-haloacetanilides.

German Offenlegungschrifft No. 2,702,102, published July 20, 1978, discloses fungicidal N-azolylacetyl-N-phenylalanines.

German Offenlegungschrifft No. 2,805,525, published Aug. 17, 1978, discloses herbicidal 2-alkenyl-chloroacetanilides.

SUMMARY OF THE INVENTION

It has now been found that N-(heterocyclyl)-methylacetanilides are effective as herbicides and plant growth regulators. The compounds are generally herbicidal in both pre- and post-emergent applications against weed grasses as well as broad-leaved weeds. Some compounds are selective with respect to the type of application and/or type of weed.

DESCRIPTION OF THE INVENTION

This invention relates to N-(heterocyclyl)-methylacetanilides and their use as herbicides and plant growth regulators. More specifically, this invention relates to herbicidal compounds represented by the formula

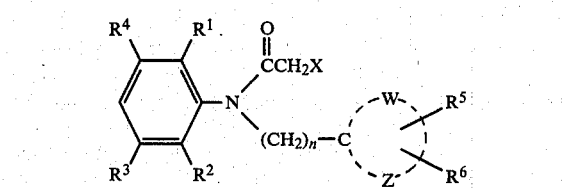

wherein $R^1$ is alkyl of 1 to 6 carbon atoms, alkoxy of 1 to 6 carbon atoms, alkenyl of 1 to 6 carbon atoms, haloalkyl of 1 to 2 carbon atoms and 1 to 3 of the same or different halogens selected from fluoro, chloro, bromo or iodo, nitro, hydroxy, alkoxyalkyl of 2 to 6 carbon atoms, fluoro, bromo, chloro or iodo, $R^2$, $R^3$ and $R^4$ are independently selected from hydrogen, alkyl of 1 to 6 carbon atoms, alkoxy of 1 to 6 carbon atoms, alkenyl of 1 to 6 carbon atoms, haloalkyl of 1 to 2 carbon atoms and 1 to 3 of the same or different halogens selected from fluoro, chloro, bromo or iodo, nitro, hydroxy, alkoxyalkyl of 2 to 6 carbon atoms, fluoro, bromo, chloro or iodo; $R^5$ and $R^6$ are independently selected from hydrogen, alkyl of 1 to 6 carbon atoms, alkoxy of 1 to 6 carbon atoms, alkenyl of 1 to 6 carbon atoms, alkoxyalkyl of 2 to 6 carbon atoms, phenyl and phenyl substituted with 1 to 5 of the same or different substituents selected from fluoro, chloro, bromo, alkyl of 1 to 4 carbon atoms or alkoxy of 1 to 4 carbon atoms; X is fluoro, bromo, chloro, iodo or alkoxy of 1 to 3 carbon atoms; W and Z are hetero atoms in an aromatic 5-membered ring independently selected from the group consisting of nitrogen, sulfur and oxygen; and n=0, 1 or 2.

Representative heterocyclic rings containing W and Z are isoxazol-5-yl, 3-methylisoxazol-5-yl, isoxazol-3-yl, isoxazol-4-yl, 2-methylthiazol-4-yl, 2-ethylthiazol-4-yl, 2-phenylthiazol-4-yl, thiazol-4-yl, thiazol-2-yl, thiazol-5-yl, 2-methylthiazol-5-yl, 3-methylthiazol-2-yl, isothiazol-3-yl, isothiazol-4-yl, isothiazol-5-yl, pyrazol-3-yl, pyrazol-4-yl, pyrazol-5-yl, imidazol-2-yl, imidazol-4-yl, imidazol-5-yl and 4-methylthiazol-2-yl.

The heterocyclic rings are preferably isoxazol-3-yl, 2-methylthiazol-4-yl, isothiazol-3-yl and isoxazol-5-yl. Most preferably, the heterocyclic ring is a thiazole, i.e., where W is sulfur and Z is nitrogen. The most preferred ring is 2-methylthiazol-4-yl.

Representative $R^1$ groups include fluoro, bromo, chloro, iodo, trifluoromethyl, methyl, ethyl, nitro, ethoxy and methoxymethyl.

Preferably $R^1$ is methyl or ethyl.

Representative $R^2$, $R^3$ and $R^4$ groups include hydrogen, fluoro, bromo, chloro, iodo, methyl, ethyl, trifluoromethyl, nitro, ethoxy and methoxymethyl.

Preferably $R^3$ and $R^4$ are hydrogen and $R^2$ is methyl or ethyl.

Preferably $R^5$ is alkyl and $R^6$ is hydrogen. Most preferably, $R^5$ is methyl.

Preferably X is fluoro, bromo, chloro, iodo or methoxy. Most preferably X is chloro.

Preferably n is the interger 1.

The compounds of the invention can be made by reacting N-acetylanilines with a halomethyl heterocycle in substantially equimolar amounts in the presence of a strong base, such as sodium hydride, at 0° C. The reaction is carried out in a dry, inert organic solvent, preferably dimethylformamide or dimethoxyethane. The product of the invention is isolated from the reaction mixture and purified by conventional procedures such as extraction, distillation, chromatography, crystallization, etc.

The general reaction for making compounds of the invention is as follows:

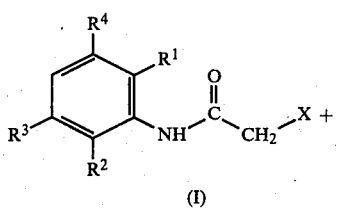

(I)

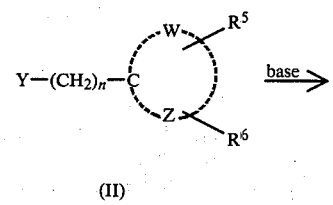

(II)

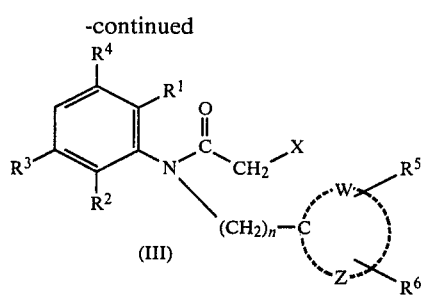

(III)

wherein $R^1$, $R^2$, $R^3$, $R^4$, $R^5$, $R^6$, X, W, Z and n have the same meaning as previously defined and Y is bromo, chloro or iodo.

The acetamide compound of the formula (I) can be prepared by conventional methods by acetylation of the selected aniline.

The haloalkyl heterocyclic intermediate of the formula (II) can generally be prepared by halogenation by conventional methods of a commercially available alkyl heterocycle or hydroxyalkyl heterocycle. For example, a methyl heterocycle can be conventionally treated with N-bromosuccinimide or a hydroxymethyl heterocycle can be treated with $SOCl_2$ to give corresponding bromomethyl or chloromethyl heterocycles.

Alternatively, intermediates of the formula (II) can be prepared by condensation reactions. In one modification of such a reaction, 1,3-dichloroacetone is condensed with an equimolar amount of thioacetamide in acetone at 0° C. to give 4-chloromethylthiazole. In general, haloalkyl heterocycles of the formula (II) are known.

An alternative sequence for making the compounds of the invention is as follows:

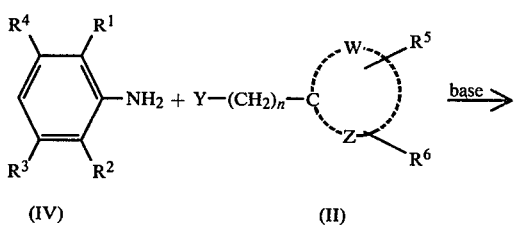

(IV)     (II)

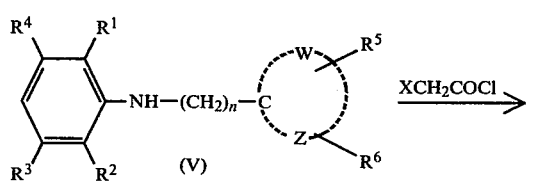

(V)

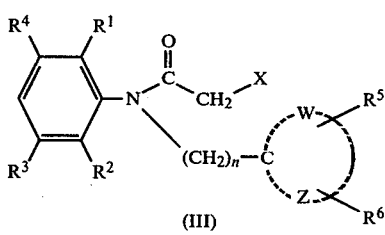

(III)

wherein $R^1$, $R^2$, $R^3$, $R^4$, $R^5$, $R^6$, X, W, Z and n have the same meaning as previously defined.

The alkylation reaction for preparing the intermediate of the formula (V) is preferably conducted at about 75°–100° C. using substantially equimolar amounts of reactants (IV) and (II) in the presence of a base such as potassium carbonate and, optionally, also in the presence of sodium iodide. The reaction is carried out in a dry, inert, organic solvent, preferably dimethylformamide or dimethoxyethane.

The acetylation of compounds of the formula (V) to obtain the product (III) can be carried out in a conventional manner by refluxing with a haloacetyl chloride in a suitable solvent, preferably toluene, until the reaction is complete.

The compounds of the present invention are, in general, herbicidal in both pre- and post-emergent applications. For pre-emergent control of undesirable vegetation, the herbicidal compounds will be applied in herbicidally effective amounts to the locus or growth medium of the vegetation, e.g., soil infested with seeds and/or seedlings of such vegetation. Such application will inhibit the growth of or kill the seeds, germinating seeds and seedlings. For post-emergent applications, the herbicidal compounds will be applied directly to the foilage and other plant parts. Generally, the herbicidal compounds of the invention are effective against weed grasses as well as broadleaved weeds. Some may be selective with respect to the type of application and/or type of weed.

The compounds, when applied to growing plants above the ground in such an amount that the compounds will not kill beneficial plants, also show efficient plant growth regulating or retarding effects and may be advantageously employed, for example, to prevent or retard the growth of lateral buds in plants and to promote the thinning out of superfluous fruits in various fruit trees.

The compounds of the present invention can be used alone as herbicides. However, it is generally desirable to apply the compounds in herbicidal compositions comprising one or more of the herbicidal compounds intimately admixed with a biologically inert carrier. The carrier may be a liquid diluent or a solid, e.g., in the form of dust powder or granules. In the herbicidal composition, the active herbicidal compounds can be from about 0.01 to 95% by weight of the entire composition.

Suitable liquid diluent carriers include water and organic solvents, e.g., hydrocarbons such as benzene, toluene, kerosene, diesel oil, fuel oil, and petroleum naphtha. Suitable solid carriers are natural clays such as kaolinite, atalpulgite, and montmorillonite. In addition, talcs, pyrophillite, diatomaceous silica, synthetic fine silicas, calcium aluminosilicate and tricalcium phosphate are suitable carriers. Organic materials such as walnut-shell flour, cottonseed hulls, wheat flour, wood flour or redwood-bark flour may also be used as solid carriers.

The herbicidal composition will also usually contain a minor amount of a surface-active agent. Such surface agents are those commonly known as wetting agents, dispersing agents and emulsifying agents, and can be anionic, cationic or nonionic in character. The herbicidal compositions may also contain other pesticides, adjuvants, stabilizers, conditioners, fillers, and the like.

The amount of herbicidal compound or composition administered will vary with the particular plant part or plant growth medium which is to be contacted, the general location of application—i.e., sheltered areas such as greenhouses, as compared to exposed areas such as fields—as well as the desired type of control. Generally, for both pre- and post-emergent control, the herbicidal compounds of the invention are applied at rates of 0.2 to 60 kg/ha, and the preferred rate is in the range 0.5 to 40 kg/ha.

For plant growth regulating or retarding activity, it is essential to apply the compounds of the invention at a concentration not so high as to kill the plants. Therefore, the application rates for plant growth regulating or retarding activity will generally be lower than the rates used for killing the plants. Generally, such rates vary from 0.1 to 5 kg/ha, and preferably from 0.1 to 3 kg/ha.

Pre- and post-emergent herbicidal and plant growth regulating tests on representative compounds of the invention were made using the following methods:

Pre-Emergent Test

An acetone solution of the test compound was prepared by mixing 750 mg of the compound, 220 mg of a nonionic surfactant and 25 ml of acetone. This solution was added to approximately 125 ml of water containing 156 mg of surfactant.

Seeds of the test vegetation were planted in a pot of soil and the test solution was sprayed uniformly onto the soil surface at a dose of 33 micrograms/cm$^2$. The pot was watered and placed in a greenhouse. The pot was watered intermittently and was observed for seedling emergence, health of emerging seedlings, was observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests appear in Table I.

Pre-Emergence Test

The test compound was formulated in the same manner as described above for the pre-emergent test. The concentration of the test compound in this formulation was 5000 ppm. This formulation was uniformly sprayed on 2 similar pots of 24-day-old plants (approximately 15 to 25 plants per pot) at a dose of 33 micrograms/cm$^2$. After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill. The results of these tests appear in Table I.

AXILLARY BUD GROWTH INHIBITION OF PINTO BEAN PLANTS

Compound Nos. 3 and 13 were tested to determine their plant-growth-retarding effects on axillary bud growth of pinto beans.

Idaho pinto bean plants (13-16 days old) having monofoliate leaves fully developed and first trifoliates beginning to unfold were used. All growth 5 mm above the monofoliate leaf node was removed with forceps 1 to 4 hours prior to treatment with the test compounds. Four plants were used for each test compound.

A 625-ppm solution of the test compound in a 2% aqueous acetone solution containing a small amount of a non-ionic surfactant was sprayed onto the pinto bean plants until runoff. After drying, the treated plants were transferred to a greenhouse maintained at 20°-23° C. and watered at regular intervals. Twelve days after treatment, the bud growth at the axil of the monofoliate leaf was determined and expressed as percent inhibition of axillary bud growth as compared to untreated check plants. The percent inhibition for Compound No. 3 was 90% and for Compound 13 was 70%.

TABLE I

Herbicidal Effectiveness of compounds of the formula

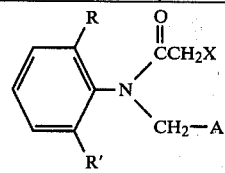

| No. | R | R' | X | A | Pre/Post[1] L | M | P | C | W | O |
|---|---|---|---|---|---|---|---|---|---|---|
| 1 | Me | Me | Cl | (isoxazole-CH₃) | — | — | — | 95/0 | 100/0 | 95/0 |
| 2 | Me | Me | Cl | (isoxazoline) | 40/10 | 10/0 | 95/30 | 100/85 | 100/85 | 94/15 |
| 3 | Me | Me | Cl | (thiazole-CH₃) | 93/40 | 78/40 | 88/35 | 100/60 | 100/85 | 93/70 |
| 4 | H | H | Cl | (isoxazoline) | 60/30 | 60/30 | 60/10 | 30/0 | 98/0 | — |
| 5 | Me | Me | Cl | (isothiazoline) | 75/0 | 75/0 | 95/0 | 100/85 | 100/80 | 95/35 |
| 6 | Et | Et | Cl | (isoxazole-CH₃) | — | — | — | — | 0/20 | — |

TABLE I-continued

Herbicidal Effectiveness of compounds of the formula

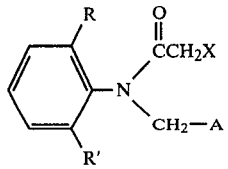

| | | | | | Pre/Post[1] | | | | | |
|---|---|---|---|---|---|---|---|---|---|---|
| No. | R | R' | X | A | L | M | P | C | W | O |
| 7 | Me | H | Cl | (isoxazole) | — | 15/0 | 40/0 | 60/0 | 100/55 | — |
| 8 | Me | H | Cl | (methyl-isoxazole) | — | — | — | — | 85/0 | — |
| 9 | Et | Et | Cl | (methyl-thiazole) | — | 20/0 | 25/0 | 95/60 | 100/80 | 95/45 |
| 10 | Me | H | Cl | (isoxazole) | — | — | — | 25/0 | 100/0 | — |
| 11 | Et | Et | Cl | (isoxazole) | — | 25/0 | 50/0 | 90/45 | 97/70 | 85/30 |
| 12 | Et | Et | Cl | (isoxazole) | — | — | 45/10 | 95/50 | 100/70 | 95/30 |
| 13 | Et | Me | Cl | (methyl-thiazole) | 98/25 | 75/15 | 30/15 | 100/35 | 100/85 | 100/70 |
| 14 | Et | Me | Cl | (thiazole) | 60/35 | 70/25 | 95/30 | 97/75 | 97/83 | 95/75 |
| 15 | Et | Me | Cl | (methyl-thiazole) | — | — | — | 95/0 | 100/0 | 40/0 |
| 16 | Et | Me | OCH$_3$ | (thiazole) | 30/30 | 15/25 | 70/20 | 95/40 | 97/65 | 50/10 |

[1]Data are based on a scale of 0-100 at application of 33 micrograms cm/[2], as explained above. Upper figure is the pre-emergent test result, lower figure is the post-emergent test result.
Blank entries represent a 0/0 result.
L = Lambsquarter (*Chenopodium album*)
M = Mustard (*Brassica arvensis*)
P = Pigweed (*Amaranthus retroflexus*)
C = Crabgrass (*Digitaria sanguinalis*)
W = Watergrass (*Echinochloa crusgalli*)
O = Wild Oats (*Avena fatua*)

EXAMPLES

Example 1—Preparation of 3-methylisothiazole

A solution of 40% sodium hydroxide was added dropwise to an aqueous solution containing 30 g (0.2 mol) 3-methyl-5-aminoisothiazole hydrochloride until neutral. The solution was extracted with methylene chloride and the extract was dried and stripped to yield 17.85 g free 3-methyl-5-aminoisothiazole. To 85 ml concentrated sulfuric acid cooled to 0° C. was added 11.97 g sodium nitrite. While maintaining this solution at 0° C., 3-methyl-5-aminoisothiazole was added in portions over a 45-minute period, after which the solution was stirred for 1 hour at 0° C. This solution was then added slowly over a 1-hour period at −10° C. to a stirred solution of 285 ml of 30% hypophosphorous acid containing 0.63 g cuprous oxide. When addition was complete, the mixture was allowed to reach room temperature and brought to pH 9 by adding 20% sodium hydroxide. Methylene chloride was added and the mixture was allowed to stand overnight. The mixture was extracted with methylene chloride and was then dried and fractionally distilled at atmospheric pressure. 3-Methylisothiazole distilled at approximately 130° C. Yield: 5.5 g (35%).

Example 2—Preparation of 3-bromomethylisothiazole

A mixture containing 14.5 g 3-methylisothiazole (prepared as in Example 1 above) and 26 g N-bromosuccinimide in carbon tetrachloride was heated to reflux temperature and photolyzed with a sun lamp for 24 hours. The mixture was cooled and filtered. The liquid residue was stripped on an aspirator and distilled under vacuum. The fraction taken at 96° C. at 15 mm pressure was cooled, diluted with ether, and filtered. The ether was stripped and 2.5 g (6.65%) 3-bromomethylisothiazole was obtained.

Example 3—Preparation of 2-chloro-N-(isothia-(zol-3-yl)methyl-N-(2,6-dimethylphenyl)acetamide To a mixture of 4.34 g N-chloroacetyl-2,6-dimethylaniline and 4.0 g 3-bromomethylisothiazole (prepared in Example 2 above) in 100 ml dry dimethylformamide was added 1.1 g sodium hydride at 0° C. The mixture was stirred overnight and allowed to reach room temperature and filtered. The solvent was stripped and the residue dissolved in methylene chloride, washed with water, dried and stripped of solvent. The crystalline product was obtained after slurrying in hexane. M.p.=84°-88° C. The product is shown as Compound 5 in Table I. $C_{14}H_{15}ClN_2OS$: calc., %C 57.05, %H 5.09, %N 9.51; found, %C 57.81, %H 5.4, %N 9.38.

Example 4—Preparation of 2-methyl-4-chloromethylthiazole

A. Thionyl chloride, 21.6 ml (35.3 g) was added dropwise to a solution of 38 g 2-methyl-4-hydroxymethylthiazole in 200 ml dry chloroform. The solution was refluxed for 3 hours, cooled, and the solvent and HCl stripped. The residue was dissolved in 200 ml methylene chloride, cooled to 0° C. and neutralized with one equivalent sodium bicarbonate in 400 ml ice water. The methylene chloride phase was separated, dried, stripped of solvent and distilled to yield 20.8 g 2-methyl-4-chloromethylthiazole (colorless liquid).

B. To a solution of 12.7 g dichloroacetone in acetone was added a solution of 7.5 g thioacetamide in 40 ml acetone at ice-bath temperature. The mixture was stirred overnight and filtered. The solid residue was stripped of acetone, slurried in benzene and heated to reflux temperature. After no more HCl evolved, the solvent was stripped to yield 2g 2-methyl-4-chloromethylthiazole.

Example 5—Preparation of 2-chloro-N-(2-methylthiazol-4-yl)methyl-N-(2,6-dimethylphenyl)acetamide A mixture of 5.33 g N-chloroacetyl-2,6-dimethylaniline and 4 g 2-methyl-4-chloromethylthiazole (prepared in Example 4A above) in dry dimethylformamide was treated with 1.56 g sodium hydride as in Example 3 above. After workup, the solid product was purified by high-pressure liquid chromatography to yield 1.5 g pure product, m.p. 62°-64° C. This product is shown as Compound 3 in Table I. $C_{15}H_{17}ClN_2OS$: calc., %C 58.35, %H 5.51, %N 9.08; found, %C 59.23, %H 5.79, %N 9.28.

Example 6—Preparation of 3-bromomethylisoxazole

A mixture of 8.3 g 3-methylisoxazole and 17.7 g N-bromosuccinimide in carbon tetrachloride was heated to reflux and irradiated for 4 hours with benzyl peroxide as an initiator. The mixture was stirred overnight, filtered and the solvent stripped from the liquid residue. 6 g of 3-bromomethylisoxazole was recovered.

Example 7—Preparation of 2-chloro-N-(isoxazol-3-yl)methyl-N-(2,6-dimethylphenyl)acetamide A mixture of 6.1 g N-chloroacetyl-2,6-dimethylaniline and 5 g 3-bromomethylisoxazole (prepared as in Example 6 above) in 200 ml dry dimethylformamide was treated with 1.5 g sodium hydride as in Example 3 above. After workup, the solid product was purified by column and high-pressure liquid chromatography to yield a pure product, m.p. 78°-81° C. This product is shown as Compound 2 in Table I. $C_{14}H_{15}ClN_2O_2$: calc., %C 60.32, %H 5.39, %N 10.05; found, %C 60.72, %H 5.71, %N 8.85.

Example 8—Preparation of 3-methyl-5-chloromethylisoxazole

A solution of 100 ml benzene, 20 g 3-methyl-5-hydroxymethylisoxazole and 32 g thionyl chloride was stirred and heated to reflux. After 2 hours of refluxing, the mixture was stripped of solvent and distilled under vacuum. 3-Methyl-5-chloromethylisoxazole was recovered as a yellow liquid, b.p. 40°-42° C. at 0.6 mm Hg.

Example 9—Preparation of 2-chloro-N-(3-methylisoxazol-5-yl)methyl-N-(2,6-dimethylphenyl)acetamide A mixture of 4.54 g N-chloroacetyl-2,6-dimethylaniline and 3 g 3-methyl-5-chloromethylisoxazole (prepared as in Example 8 above) in 100 ml dry dimethylformamide was treated with 1.33 g sodium hydride as in Example 3 above. After workup, the solid product was purified by column and high-pressure liquid chromatography to yield 2.0 g pure product, m.p. 78°-82° C. This product is shown as Compound 1 in Table I. $C_{15}H_{17}ClN_2O_2$: calc., %C 61.54, %H 5.81, %N 9.57; found, %C,63.37, %H 6.16, %N 9.65.

Example 10—Preparation of 4-chloromethylthiazole

To 50 g formamide dissolved in 400 ml THF was added 50 g $P_2S_5$ while maintaining the temperature at 30°-35° C. The mixture was stirred for 6 hours at room temperature, filtered and stripped of THF. The crude product was suspended in 175 ml ethyl acetate and cooled at dry-ice temperature overnight, filtered and dried in vacuo at room temperature to give 26.5 g thioformamide.

The thioformamide was slurried in 50 ml acetone and added to 55.17 g 1,3-dichloroacetone in 25 ml acetone. The temperature was kept below 10° C. and stirred overnight. The solvent was stripped and 200 ml methanol were added. To this mixture 15.2 g zinc chloride was added in portions. After 30 minutes stirring, the methanol was stripped and the product was added to a water-methylene chloride mixture and neutralized with saturated sodium bicarbonate solution. The emulsion was filtered through Celite and the methylene chloride layer was collected, dried, stripped and distilled. B.p., 57°-62° C. The distillate was dissolved in ether and HCl was bubbled through it for 15 minutes. The resulting white precipitate was filtered off, dissolved in water and neutralized with sodium bicarbonate. The aqueous solution was extracted four times with methylene chloride. The methylene chloride extracts were stripped to yield 10.2 g 4-chloromethylthiazole.

Example 11—Preparation of N-(thiazol-4-yl)methyl-2-ethyl-6-methylaniline

In 200 ml dry dimethylformamide was added 10.2 g 4-chloromethylthiazole, 10.26 g 2-ethyl-6-methylaniline and 10.54 g of potassium carbonate. The mixture was stirred at 100° C. for 3 days and filtered. The filtrate was stripped, dissolved in methylene chloride, washed with water, dried and stripped again. The crude product was chromatographed with methylene chloride through a 200-g silica-gel column to give 7 g of product.

Example 12—Preparation of 2-chloro-N-(thiazol-4-yl)methyl-N-(2-ethyl-6-methylphenyl)acetamide A mixture of 3.5 g N-(thiazol-4-yl)methyl-2-ethyl-6-methylaniline (from Example 11) and 125 ml toluene was heated to reflux and 1.7 g chloroacetyl chloride was added dropwise. The mixture was refluxed for 2 hours, cooled, stripped and purified on a silica-gel column using methylene chloride followed by 2% methanol:methylene chloride. $C_{15}H_{17}ClN_2O_5$: calc., %C 58.35,%H 5.51, %N, 9.08; found, %C 57.07, %H 5.58, %N 7.81.

Example 13—Preparation of N-(2-phenyl)-thiazol-4-yl)methyl-2-ethyl-6-methylaniline A mixture of 28.42 g 2-ethyl-6-methylaniline, 43.89 g 2-phenyl-4-chloromethylthiazole and 29 g potassium carbonate in 400 ml dry dimethylformamide was stirred at 100° C. for 5 days. The mixture was worked up and purified as in Example 11 and further purified by high-pressure liquid chromatography. 6 g of product was obtained.

Example 14—Preparation of 2-chloro-N-(2-phenyl-thiazol-4-yl)-methyl-(2-ethyl-6-methylphenyl)acetamide A mixture of 3.3 g of the product obtained in Example 13 in 125 ml toluene was treated as in Example 12 above. 2 g white solid was obtained. M.p., 88°–90° C.

$C_{21}H_{21}ClN_2OS$ calc., %C 65.54, %H 5.46, %N 7.28; found, %C 66.31, %H 5.64, %N 7.82.

What is claimed is:

1. The compound of the formula

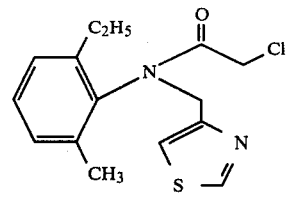

2. An herbicidal composition comprising an herbicidally effective amount of a compound defined in claim 1 and a biologically inert carrier.

3. A method for controlling undesirable vegetation which comprises applying to said vegetation or its growth medium an herbicidally effective amount of a compound defined in claim 1.

4. A plant-growth-regulating composition comprising a biologically inert carrier and a plant-growth-regulating amount of the compound of the formula defined in claim 1.

5. A method for regulating plant growth which comprises applying to said plants or their growth environment a plant-growth-retarding amount of the compound of the formula defined in claim 1.

* * * * *